(12) United States Patent
Mou et al.

(10) Patent No.: US 11,067,557 B2
(45) Date of Patent: Jul. 20, 2021

(54) GAS DETECTING DEVICE (71) Applicant: Microjet Technology Co., Ltd., Hsinchu (TW)

(72) Inventors: Hao-Jan Mou, Hsinchu (TW); Ta-Wei Hsueh, Hsinchu (TW); Shih-Chang Chen, Hsinchu (TW); Li-Pang Mo, Hsinchu (TW); Yung-Lung Han, Hsinchu (TW); Chi-Feng Huang, Hsinchu (TW); Wei-Ming Lee, Hsinchu (TW); Chun-Yi Kuo, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 267 days.

(21) Appl. No.: 16/198,370

(22) Filed: Nov. 21, 2018

(65) Prior Publication Data

US 2019/0170717 A1    Jun. 6, 2019

(30) Foreign Application Priority Data

Dec. 4, 2017 (TW) ................................ 106142411

(51) Int. Cl.
*G01N 33/00* (2006.01)
(52) U.S. Cl.
CPC ..... *G01N 33/0062* (2013.01); *G01N 33/0031* (2013.01); *G01N 33/0036* (2013.01)
(58) Field of Classification Search
CPC ................................................ G01N 33/0062
USPC ....................................................... 702/24
See application file for complete search history.

(56) References Cited

U.S. PATENT DOCUMENTS

| 5,933,245 A | 8/1999 | Wood et al. |
| 6,104,127 A | 8/2000 | Kameyama et al. |
| 6,165,347 A | 12/2000 | Warburton |
| 6,839,636 B1 * | 1/2005 | Sunshine ............... B82Y 15/00 |
| | | 422/82.01 |
| 2008/0159341 A1 | 7/2008 | Patel et al. |

(Continued)

FOREIGN PATENT DOCUMENTS

| CN | 107037178 A | 8/2017 |
| TW | 201719147 A | 6/2017 |
| TW | M543870 U | 6/2017 |

OTHER PUBLICATIONS

Indian Office Action for Indian Application No. 201824043828, dated Jan. 14, 2021, with English translation.

*Primary Examiner* — Ricky Go
(74) *Attorney, Agent, or Firm* — Birch, Stewart, Kolasch & Birch, LLP (57) ABSTRACT

A gas detecting device includes an actuating-and-sensing module, a driving controller, a data storage device and a data processor. The actuating-and-sensing module includes a first gas sensor, a second gas sensor and a gas transportation actuator. The driving controller controls the actuations and non-actuations of the first gas sensor, the second gas sensor and the gas transportation actuator. The first gas sensor measures the target gas and transmits first gas measured information to the data storage device. The second gas sensor measures the target gas and transmits second gas measured information to the data storage device. The data processor calculates concentrations of the gases in the target gas by comparing the information stored in a gas database, the first gas measured information and the second gas measured information.

18 Claims, 11 Drawing Sheets

(56) References Cited

U.S. PATENT DOCUMENTS

| | | |
|---|---|---|
| 2010/0229658 A1 | 9/2010 | Glezer et al. |
| 2011/0257897 A1* | 10/2011 | Watanabe ............ G01N 27/128 |
| | | 702/23 |
| 2014/0377099 A1 | 12/2014 | Hsueh et al. |
| 2016/0258897 A1* | 9/2016 | Sakakibara ............ G01N 27/41 |

* cited by examiner

GAS DETECTING DEVICE

FIELD OF THE INVENTION

The present disclosure relates to a gas detecting device, and more particularly to a gas detecting device capable of measuring a concentration of target gas without separating the target gas from a gas mixture.

BACKGROUND OF THE INVENTION

Nowadays, people pay much attention to the gas information. However, it is very difficult to detect the gas. In particular, the gas in the normal state often exists as a gas mixture containing a plurality of gases. When target gas is measured, it is often interfered by other gas, which may result in inaccurate measuring results or failure. At present, in order to prevent the gas to be measured from being interfered by other gases, the gas to be measured may be separated from the gas mixture before detection begins. However, it is very difficult to separate the gas to be measured from the gas mixture, and the cost is high. Moreover, a gas separation device is difficult to be miniaturized and is not convenient to carry.

Currently, there is no equipment that can accurately measure the concentration of the target gas without separating the target gas from the gas mixture. Therefore, there is a need of providing a gas detecting device, which is safe and convenient to carry and can accurately measure the concentration of the target gas without separating the target gas from the gas mixture.

SUMMARY OF THE INVENTION

An object of the present disclosure is to provide a gas detecting device to address the issues that it is difficult to obtain an accurate measuring result of a single gas. The gas detecting device is used to measure a target gas and includes an actuating-and-sensing module, a driving controller, a data storage device and a data processor. The actuating-and-sensing module includes a first gas sensor, a second gas sensor and a gas transportation actuator. The first gas sensor has better capability for measuring first gas. The second gas sensor has better capability for measuring second gas. The gas transportation actuator guides the target gas to the first gas sensor and the second gas sensor for measurement. The driving controller controls the actuations and non-actuations of the first gas sensor, the second gas sensor and the gas transportation actuator. The data storage device has a gas database, which stores reference information relative to a gas consisting of the first gas, a gas consisting of the second gas and a gas mixture including the target gas measured by the first gas sensor, and stores reference information relative to the gas consisting of the first gas, the gas consisting of the second gas and the gas mixture including the target gas measured by the second gas sensor. The data processor calculates gas concentrations in the target gas. The first gas sensor measures the target gas and transmits first gas measured information to the data storage device. The second gas sensor measures the target gas and transmits second gas measured information to the data storage device. The data processor calculates a concentration of the first gas in the target gas by comparing the reference information stored in the gas database, the first gas measured information and the second gas measured information.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
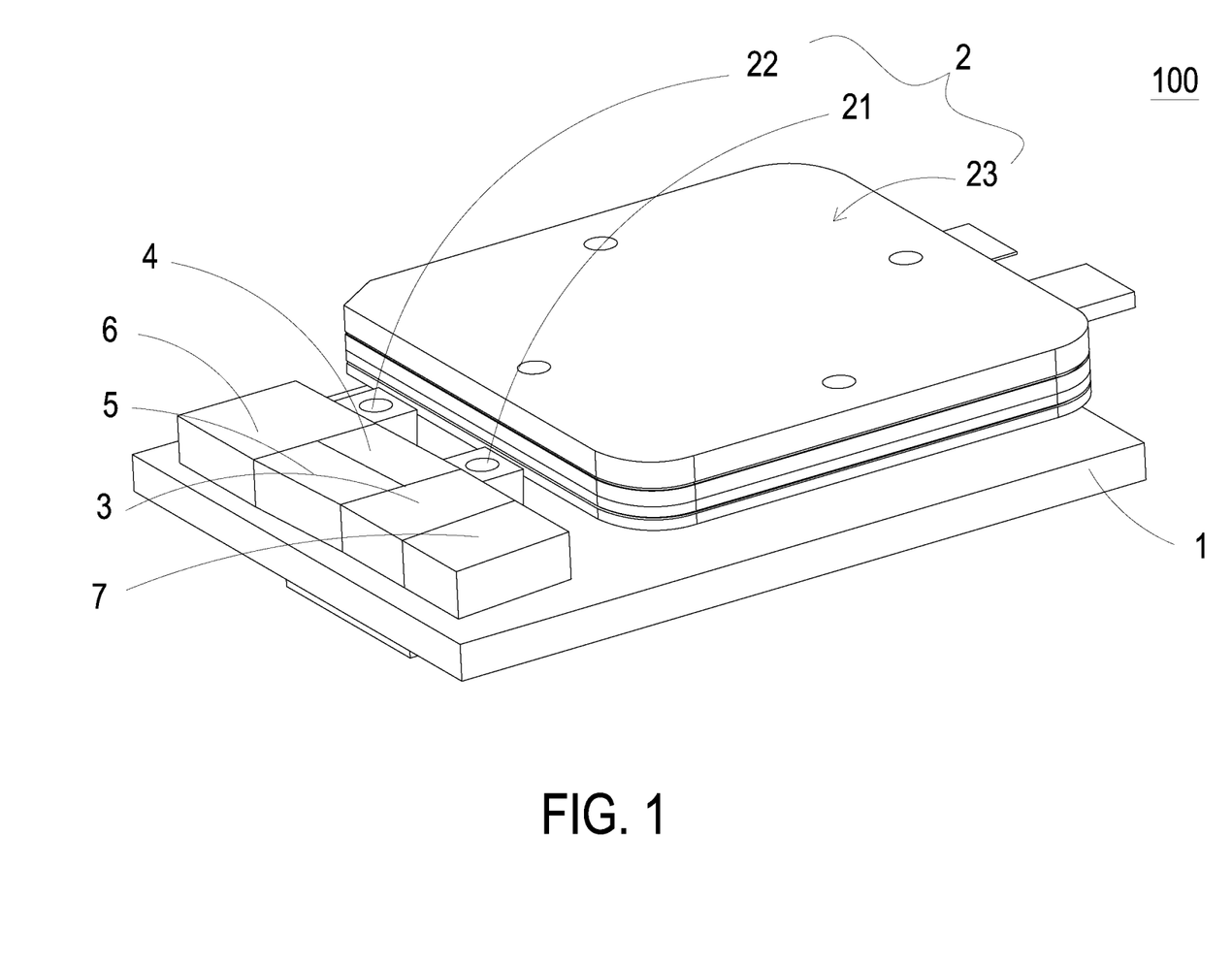
FIG. 1 is a schematic perspective view illustrating a gas detecting device according to an embodiment of the present disclosure.
Figure 2:
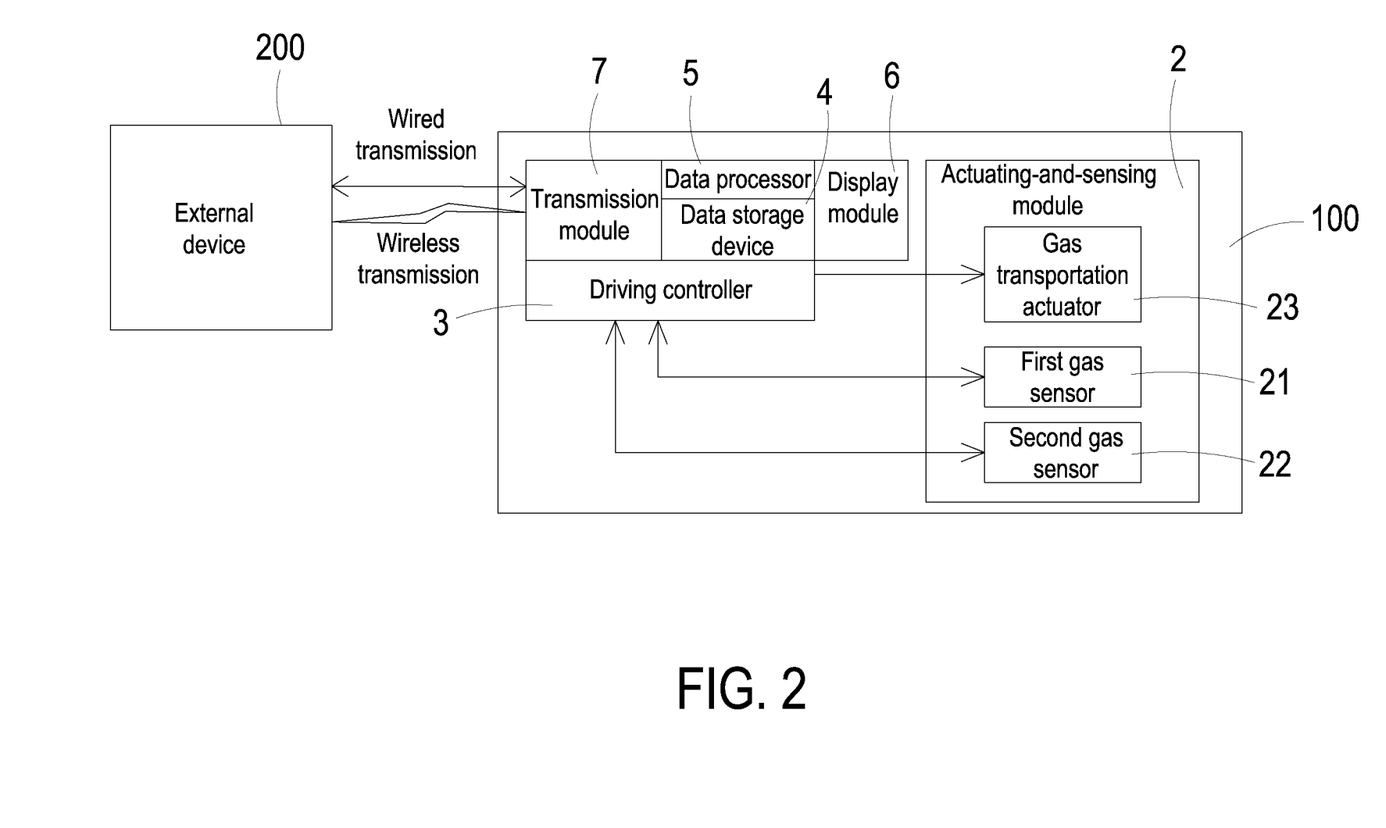
FIG. 2 schematically illustrates an architecture of the gas detecting device of the present disclosure.

Please refer to FIGS. 1 and 2. The present discourse provides a gas detecting device 100 including at least one first gas, at least one second gas, at least one target gas, at least one actuating-and-sensing module 2, at least one first gas sensor 21, at least one second gas sensor 22, at least one gas transportation actuator 23, at least one driving controller 3, at least one data storage device 4, at least one gas database, at least one data processor 5, at least one first gas measured information and at least one second gas measured information. The number of the first gas, the second gas, the target gas, the actuating-and-sensing module 2, the first gas sensor 21, the second gas sensor 22, the gas transportation actuator 23, the driving controller 3, the data storage device 4, the gas database, the data processor 5, the first gas measured information and the second gas measured information is exemplified by one for each in the following embodiments but not limited thereto. It is noted that each of the first gas, the second gas, the target gas, the actuating-and-sensing module 2, the first gas sensor 21, the second gas sensor 22, the gas transportation actuator 23, the driving controller 3, the data storage device 4, the gas database, the data processor 5, the first gas measured information and the second gas measured information can also be provided in plural numbers.

Please refer to FIGS. 1 and 2. The gas detecting device 100 of the present disclosure includes a substrate 1, an actuating-and-sensing module 2, a driving controller 3, a data storage device 4 and a data processor 5. The actuating-and-sensing module 2 is disposed on the substrate 1, and electrically connected to the driving controller 3 and the data storage device 4. The data storage device 4 is electrically connected to the data processor 5. The actuating-and-sensing module 2 includes a first gas sensor 21, a second gas sensor 22 and a gas transportation actuator 23. The gas transportation actuator 23 is disposed adjacent to the first gas sensor 21 and the second gas sensor 22, and is configured to transport the gas to the first gas sensor 21 and the second gas sensor 22 for measurement. In addition, the driving controller 3 is electrically connected to the gas transportation actuator 23, the first gas sensor 21 and the second gas sensor 22. The driving controller 3 controls the actuations and non-actuations of the gas transportation actuator 23, the first gas sensor 21 and the second gas sensor 22. The first gas sensor 21 and the second gas sensor 22 are electrically connected to the data storage device 4, respectively, and transmit the measured information of the target gas to the data storage device 4, respectively. In addition, each of the first gas sensor 21 and the second gas sensor 22 may be but not limited to a semiconductor gas sensor. The first gas sensor 21 has better capability for measuring a first gas. The second gas sensor 22 has better capability for measuring a second gas.

The data storage device 4 has a gas database (not shown). The gas database stores reference information relative to a single gas consisting of the first gas measured by the first gas sensor 21. The gas database stores reference information relative to a single gas consisting of the second gas measured by the first gas sensor 21. The gas database stores reference information relative to a gas mixture consisting of the first gas and the second gas measured by the first gas sensor 21. The gas database stores reference information relative to a gas mixture consisting of the first gas and other gases measured by the first gas sensor 21. The gas database stores reference information relative to a gas mixture consisting of the second gas and other gases measured by the first gas sensor 21. The gas database stores reference information relative to a gas mixture consisting of the first gas, the second gas and other gases measured by the first gas sensor 21. Also, the data storage device 4 stores reference information relative to the single gas consisting of the first gas measured by the second gas sensor 22. The gas database stores reference information relative to the single gas consisting of the second gas measured by the second gas sensor 22. The gas database stores reference information relative to the gas mixture consisting of the first gas and the second gas measured by the second gas sensor 22. The gas database stores reference information relative to the gas mixture consisting of the first gas and other gases measured by the second gas sensor 22. The gas database stores reference information relative to the gas mixture consisting of the second gas and other gases measured by the second gas sensor 22. The gas database stores reference information relative to the gas mixture consisting of the first gas, the second gas and other gases measured by the second gas sensor 22, but not limited thereto. The gas database further stores reference information relative to the single gas consisting of the first gas measured by the first gas sensor 21, the single gas consisting of the second gas measured by the first gas sensor 21, the gas mixture consisting of the first gas and the second gas measured by the first gas sensor 21, the gas mixture consisting of the first gas and other gases measured by the first gas sensor 21, the gas mixture consisting of the second gas and other gases measured by the first gas sensor 21, and the gas mixture consisting of the first gas, the second gas and other gases measured by the first gas sensor 21, after the gas transportation actuator 23 is actuated. The gas database 4 further stores reference information relative to the single gas consisting of the first gas measured by the second gas sensor 22, the single gas consisting of the second gas measured by the second gas sensor 22, the gas mixture consisting of the first gas and the second gas measured by the second gas sensor 22, the gas mixture consisting of the first gas and other gases measured by the second gas sensor 22, the gas mixture consisting of the second gas and other gases measured by the second gas sensor 22, and the gas mixture consisting of the first gas, the second gas and other gases measured by the second gas sensor 22, after the gas transportation actuator 23 is actuated, but not limited thereto.

Please refer to FIG. 2. When the actuating-and-sensing module 2 is actuated by the driving controller 3, the first gas sensor 21 and the second gas sensor 22 of the actuating-and-sensing module 2 transmit first gas measured information and second gas measured information to the data storage device 4, respectively. The first gas measured information transmitted from the first gas sensor 21 include gas information as the gas transportation actuator 23 is non-actuated and gas information as the gas transportation actuator 23 is actuated. The second gas measured information transmitted from the second gas sensor 22 include gas information as the gas transportation actuator 23 is non-actuated and gas information as the gas transportation actuator 23 is actuated. The data processor 5 accesses the first gas measured information and the second gas measured information from the data storage device 4 and performs a cross comparison among the information stored in the gas database, the first gas measured information and the second gas measured information so that the concentration of the first gas and the concentration of the second gas are obtained. In this embodiment, the first gas may be acetone, and the second gas may be ethanol or hydrogen, but not limited thereto.

Please refer to FIG. 1 and FIG. 2. In this embodiment, the gas detecting device 100 further includes a display module 6. The display module 6 is electrically connected to the data processor 5. After the data processor 5 calculates the concentration of the first gas and the concentration of the second gas, the display module 6 displays the concentration information of the first gas and the second gas and thus informs a user of the concentration information as well. In addition, the gas detecting device 100 also includes a transmission module 7. The transmission module 7 may be a wired transmission module or a wireless transmission module so that the concentration information of the first gas and the second gas can be transmitted to an external device 200 in wired transmission technology or wireless transmission technology. In this embodiment, the external device 200 may be at least one selected from the group consisting of a cloud system, a portable electronic device and a computer system.

As mentioned above, the wired transmission module may be at least one selected form the group consisting of a USB transmission module, a mini-USB transmission module and a micro-USB transmission module. The wireless transmission module may be at least one selected from the group consisting of a Wi-Fi transmission module, a Bluetooth transmission module, a radio frequency identification (RFID) transmission module and a near field communication (NFC) transmission module.

Figure 3A:
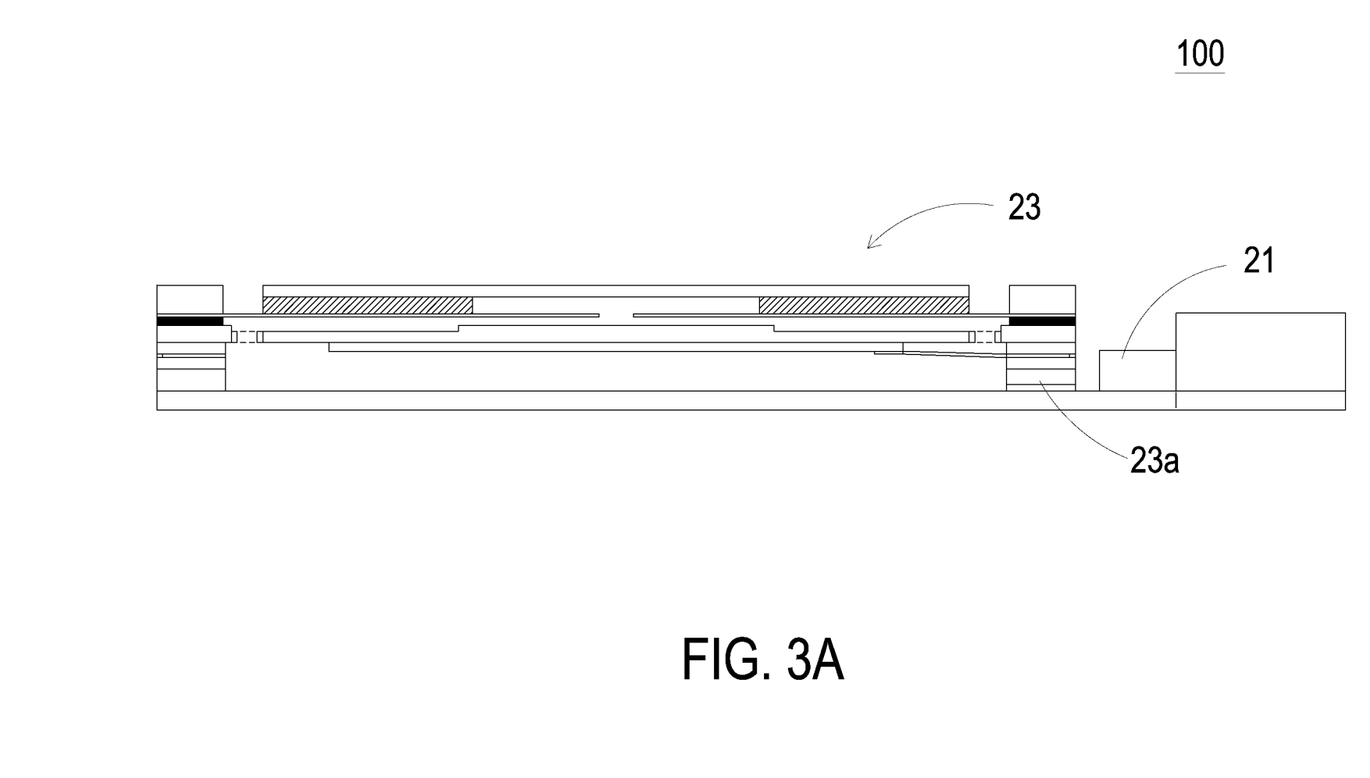
FIG. 3A is a schematic cross-sectional view illustrating the gas detecting device of the present disclosure.
Figure 3B:
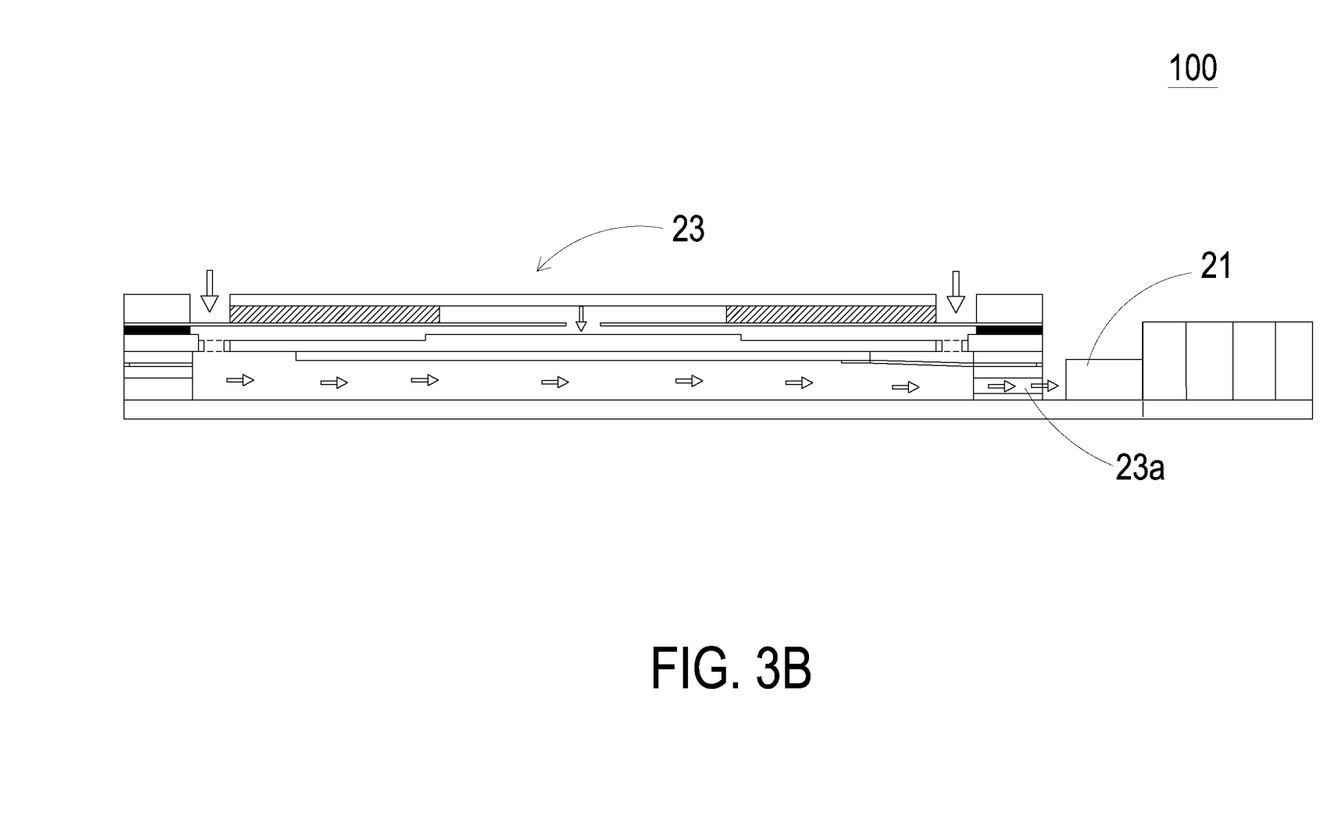
FIG. 3B schematically illustrates the actions of the gas detecting device of FIG. 3A.
Figure 4:
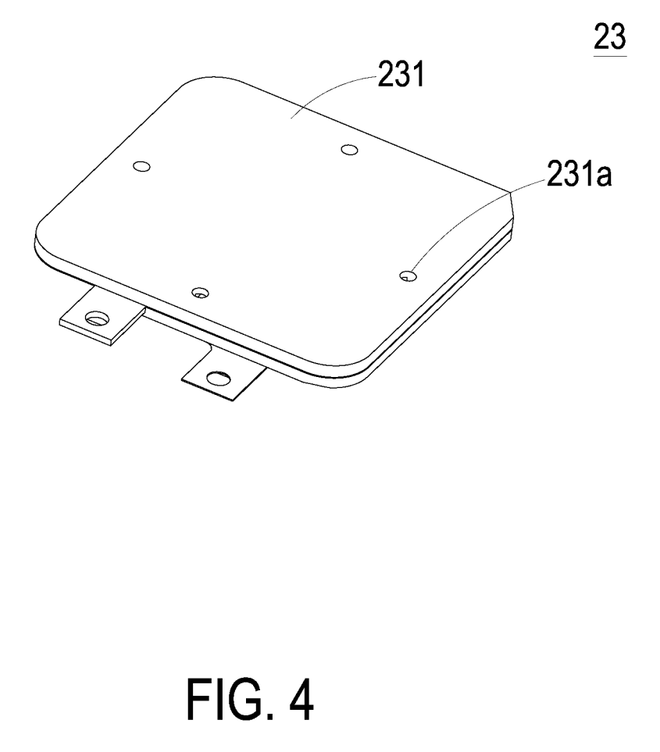
FIG. 4 is a schematic perspective view illustrating a gas transportation actuator of the gas detecting device of the present disclosure.

Please refer to FIGS. 3A, 3B and 4. In this embodiment, the gas transportation actuator 23 may be a driving structure of a piezoelectric actuating pump or a driving structure of a micro-electro-mechanical system (MEMS) pump. The gas transportation actuator 23 has an outlet aperture 23a for transporting the gas to the first gas sensor 21 and the second gas sensor 22. Hereinafter, the structures and actions of the gas transportation actuator 23 of a piezoelectric actuating pump will be described as follows.

Figure 5A:
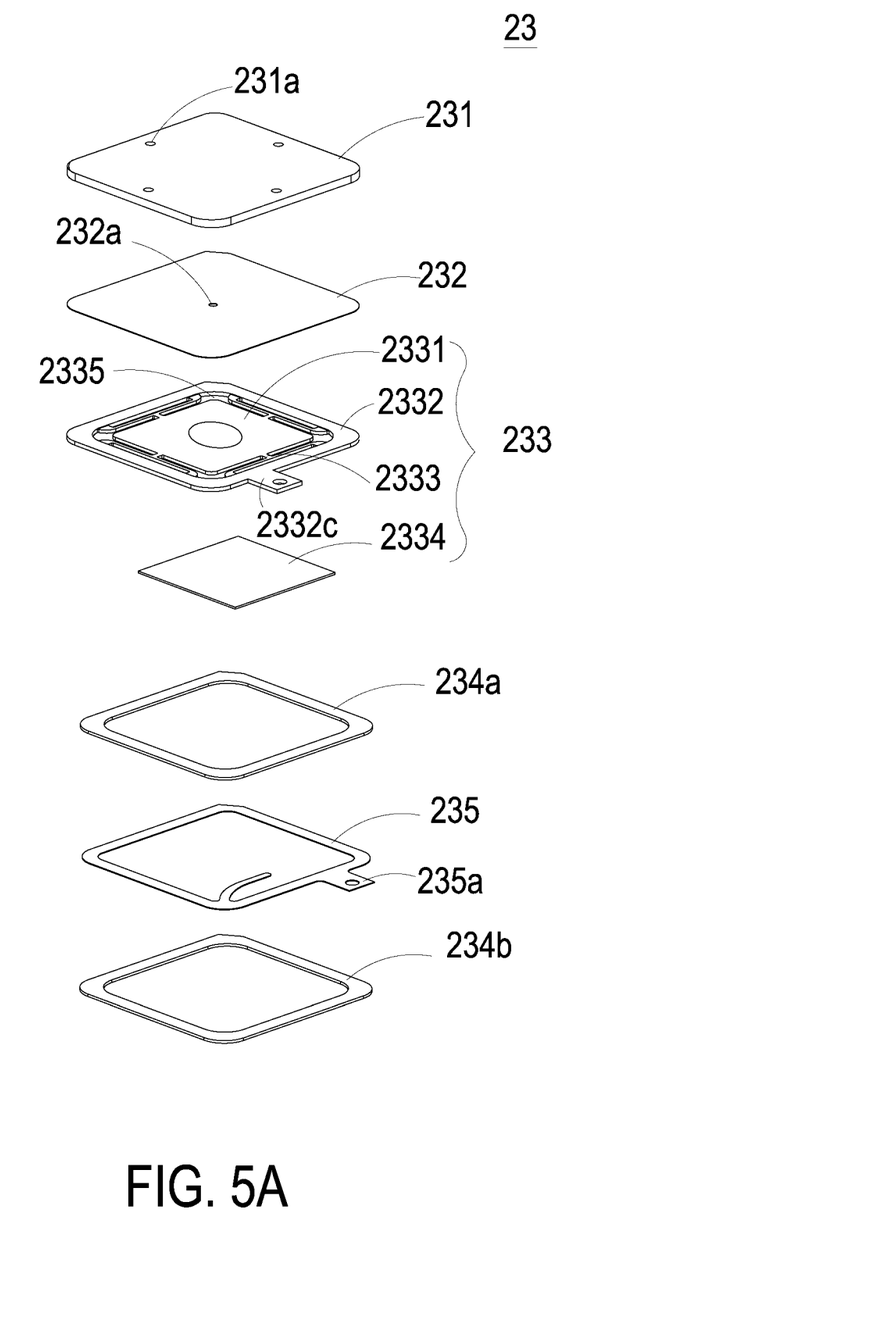
FIG. 5A is a schematic exploded view illustrating the gas transportation actuator of FIG. 4 and taken along front view.
Figure 5B:
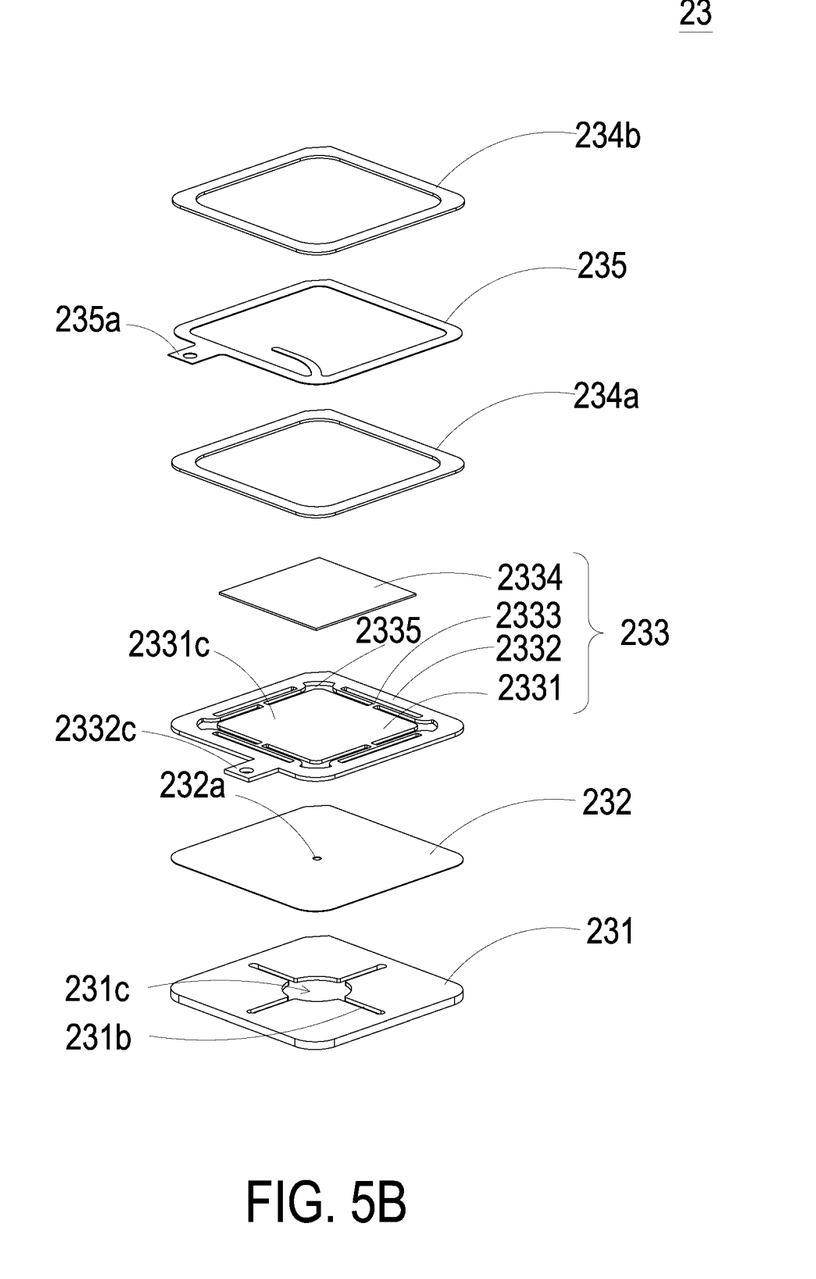
FIG. 5B is a schematic exploded view illustrating the gas transportation actuator of FIG. 4 and taken along rear view.

Please refer to FIGS. 4, 5A and 5B. The gas transportation actuator 23 includes a gas inlet plate 231, a resonance plate 232, a piezoelectric actuator 233, a first insulation plate 234a, a conducting plate 235 and a second insulation plate 234b. The piezoelectric actuator 233 is aligned with the resonance plate 232. The gas inlet plate 231, the resonance plate 232, the piezoelectric actuator 233, the first insulation plate 234a, the conducting plate 235 and the second insulation plate 234b are stacked on each other sequentially. After the above components are combined together, the cross-sectional view of the resulting structure of the gas transportation actuator 23 is shown in FIGS. 3A and 3B.

In this embodiment, the gas inlet plate 231 has at least one inlet 231a. Preferably but not exclusively, the gas inlet plate 231 has four inlets 231a. The inlets 231a run through the gas inlet plate 231. In response to the action of the atmospheric pressure, the gas can be introduced into the gas transportation actuator 23 through the at least one inlet 231a. Moreover, at least one convergence channel 231b is formed on a first surface of the gas inlet plate 231, and is corresponding in position to the at least one inlet 231a on a second surface of the gas inlet plate 231. A central cavity 231c is located at the intersection of the convergence channels 231b. The central cavity 231c is in communication with the convergence channels 231b, such that the gas from the at least one inlet 231a would be introduced into the at least one convergence channel 231b and is guided to the central cavity 231c. Consequently, the gas transportation is achieved. In this embodiment, the at least one inlet 231a, the at least one convergence channel 231b and the central cavity 231c of the gas inlet plate 231 are integrally formed from a single structure. The central cavity 231c forms a convergence chamber for temporarily storing the gas. In some embodiments, the gas inlet plate 231 may be, for example, made of stainless steel. In some other embodiments, the depth of the convergence chamber defined by the central cavity 231c may be equal to the depth of the at least one convergence channel 231b, but not limited thereto. The resonance plate 232 is made of a flexible material, but not limited thereto. The resonance plate 232 has a central aperture 232c aligned with the central cavity 231c of the gas inlet plate 231 which allows the gas to be transferred therethrough. In some other embodiments, the resonance plate 232 may be, for example, made of copper, but not limited thereto.

The piezoelectric actuator 233 includes a suspension plate 2331, an outer frame 2332, at least one bracket 2333 and a piezoelectric plate 2334. The piezoelectric plate 2334 is attached on a first surface 2331c of the suspension plate 2331. In response to an applied voltage, the piezoelectric plate 2334 is subjected to a deformation so as to drive a bending vibration of the suspension plate 2331. The at least one bracket 2333 is connected between the suspension plate 2331 and the outer frame 2332, while the two ends of the bracket 2333 are connected with the outer frame 2332 and the suspension plate 2331 respectively that the bracket 2333 can elastically support the suspension plate 2331. At least one vacant space 2335 is formed between the bracket 2333, the suspension plate 2331 and the outer frame 2332. The at least one vacant space 2335 is in communication with a gas channel for allowing the gas to go through. The type and number of the suspension plate 2331, the outer frame 2332 and the bracket 2333 may be varied according to the practical requirements. The outer frame 2332 is arranged around the suspension plate 2331. Moreover, a conducting pin 2332c is protruded outwardly from the outer frame 2332 so as to be electrically connected with an external circuit (not shown), but not limited thereto.

Figure 6:
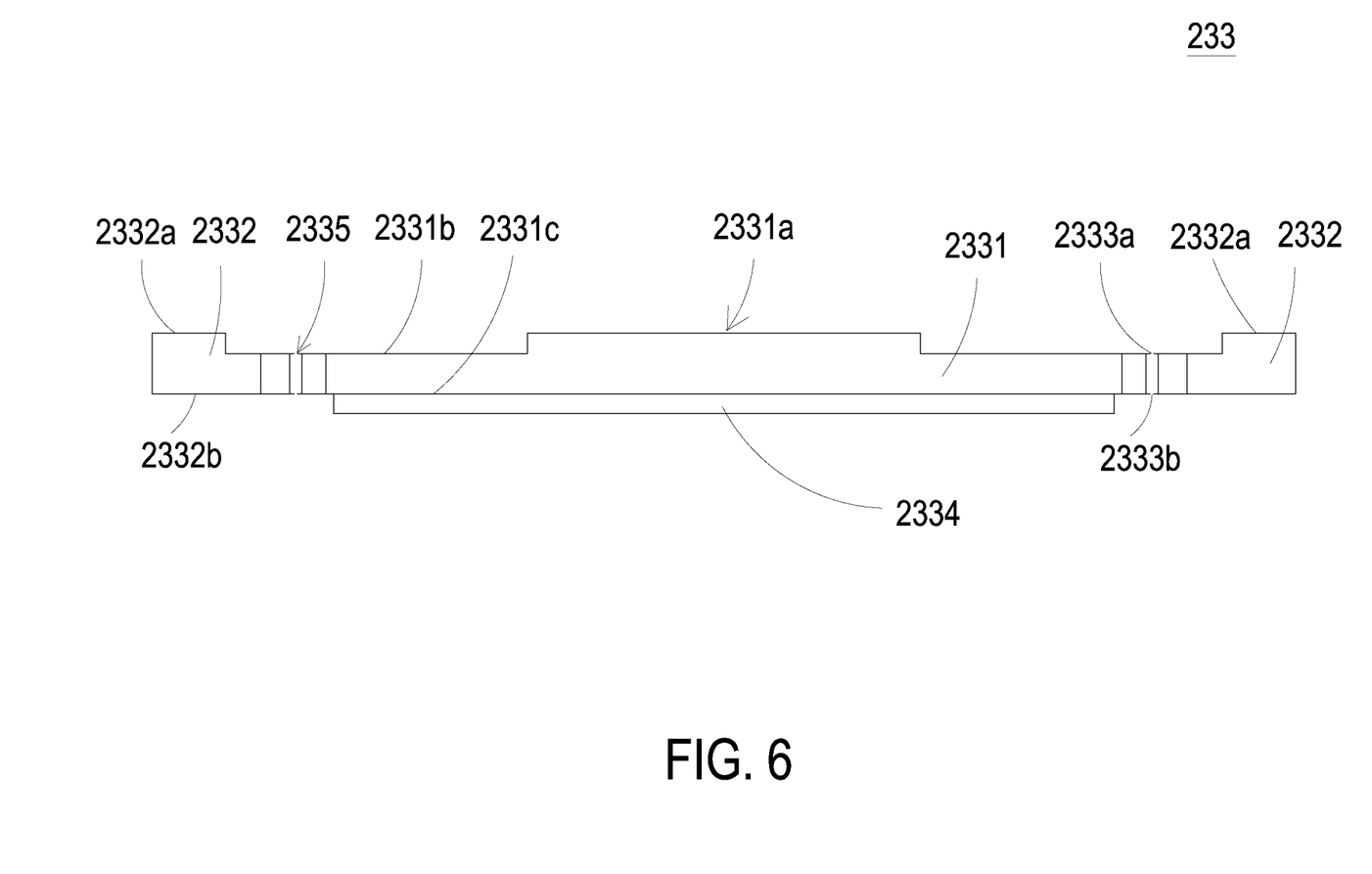
FIG. 6 is a schematic cross-sectional view illustrating the piezoelectric actuator of the gas transportation actuator as shown in FIGS. 5A and 5B.

As shown in FIG. 6, the suspension plate 2331 has a bulge 2331a that makes the suspension plate 2331 a stepped structure. The bulge 2331a is formed on a second surface 2331b of the suspension plate 2331. The bulge 2331a may be a circular convex structure. A top surface of the bulge 2331a of the suspension plate 2331 is coplanar with a second surface 2332a of the outer frame 2332, while the second surface 2331b of the suspension plate 2331 is coplanar with a second surface 2333a of the bracket 2333. Moreover, there is a specific depth from the bulge 2331a of the suspension plate 2331 (or the second surface 2332a of the outer frame 2332) to the second surface 2331b of the suspension plate 2331 (or the second surface 2333a of the bracket 2333). A first surface 2331c of the suspension plate 2331, a first surface 2332b of the outer frame 2332 and a first surface 2333b of the bracket 2333 are coplanar with each other. The piezoelectric plate 2334 is attached on the first surface 2331c of the suspension plate 2331. In some other embodiments, the suspension plate 2331 may be a square plate structure with two flat surfaces but the type of the suspension plate 2331 may be varied according to the practical requirements. In this embodiment, the suspension plate 2331, the at least one bracket 2333 and the outer frame 2332 may be integrally formed from a metal plate (e.g., a stainless steel plate). In some other embodiments, the length of a side of the piezoelectric plate 2334 is smaller than the length of a side of the suspension plate 2331. In some another embodiments, the length of a side of the piezoelectric plate 2334 is equal to the length of a side of the suspension plate 2331. Similarly, the piezoelectric plate 2334 is a square plate structure corresponding to the suspension plate 2331 in terms of the design.

In this embodiment, the first insulation plate 234a, the conducting plate 235 and the second insulation plate 234b of the gas transportation actuator 23 are stacked on each other sequentially and located under the piezoelectric actuator 233, as shown in FIG. 5A. The profiles of the first insulation plate 234a, the conducting plate 235 and the second insulation plate 234b substantially match the profile of the outer frame 2332 of the piezoelectric actuator 233. In some embodiments, the first insulation plate 234a and the second insulation plate 234b may be made of an insulating material (e.g. a plastic material) for providing insulating efficacy. In other embodiments, the conducting plate 235 may be made of an electrically conductive material (e.g. a metallic material) for providing electrically conducting efficacy. In this embodiment, the conducting plate 235 may have a conducting pin 235a disposed thereon so as to be electrically connected with an external circuit (not shown).

Figure 7:
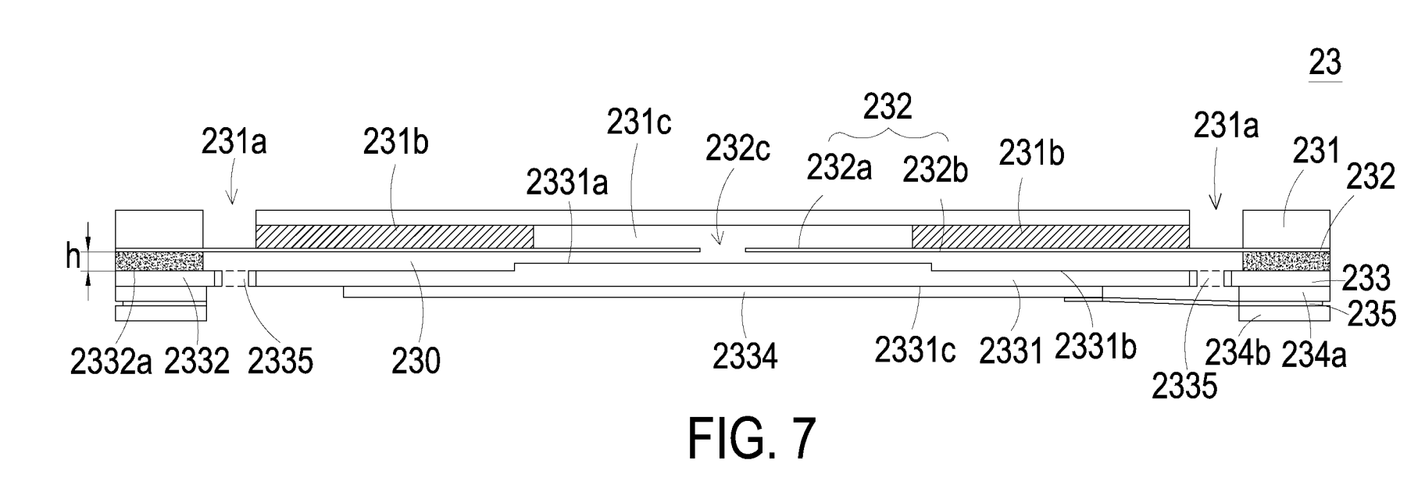
FIG. 7 is a schematic cross-sectional view illustrating the gas transportation actuator of the present disclosure.

Please refer to FIG. 7. In this embodiment, the gas inlet plate 231, the resonance plate 232, the piezoelectric actuator 233, the first insulation plate 234a, the conducting plate 235 and the second insulation plate 234b of the gas transportation actuator 23 are stacked on each other sequentially. Moreover, there is a gap h between the resonance plate 232 and the outer frame 2332 of the piezoelectric actuator 233. In this embodiment, the gap h between the resonance plate 232 and the outer frame 2332 of the piezoelectric actuator 233, may be filled with a filler (e.g. a conductive adhesive) so that a depth from the resonance plate 232 to the bulge 2331a of the suspension plate 2331 of the piezoelectric actuator 233 can be maintained. The gap h ensures the proper distance between the resonance plate 232 and the bulge 2331a of the suspension plate 2331 of the piezoelectric actuator 233, so that the gas can be transferred quickly, the contact interference is reduced and the generated noise is largely reduced. In some embodiments, alternatively, the height of the outer frame 2332 of the piezoelectric actuator 233 is increased, so that a gap is formed between the resonance plate 232 and the piezoelectric actuator 233.

Please refer to FIG. 5A, FIG. 5B and FIG. 7. After the gas inlet plate 231, the resonance plate 232 and the piezoelectric actuator 233 are combined together, a movable part 232a and a fixed part 232b of the resonance plate 232 are defined. The movable part 232a is around the central aperture 232c. The convergence chamber for converging the gas is defined by the movable part 232a of the resonance plate 232 and the gas inlet plate 231 collaboratively. Moreover, a first chamber 230 is formed between the resonance plate 232 and the piezoelectric actuator 233 for temporarily storing the gas. Through the central aperture 232c of the resonance plate 232, the first chamber 230 is in communication with the convergence chamber formed in central cavity 231c of the gas inlet plate 231. The peripheral regions of the first chamber 230 are in communication with the gas channel through the vacant space 2335 between the brackets 2333 of the piezoelectric actuator 233.

Figure 8A:
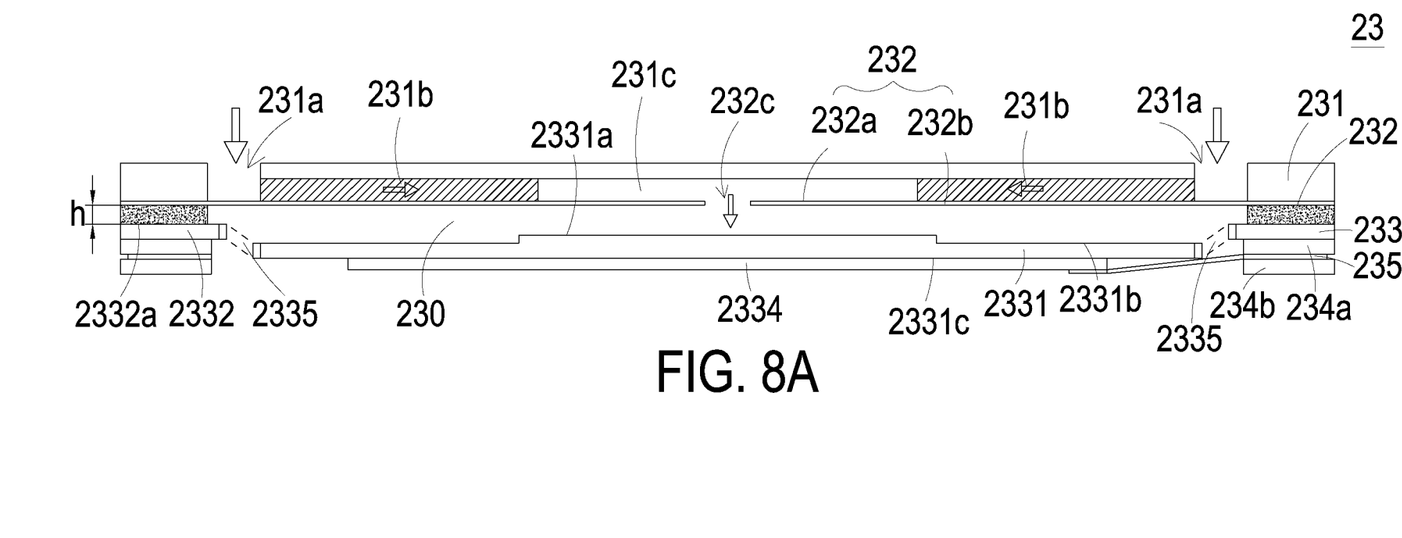
FIGS. 8A to 8E schematically illustrate the actions of the gas transportation actuator according to the embodiment of the present disclosure.
Figure 8B:
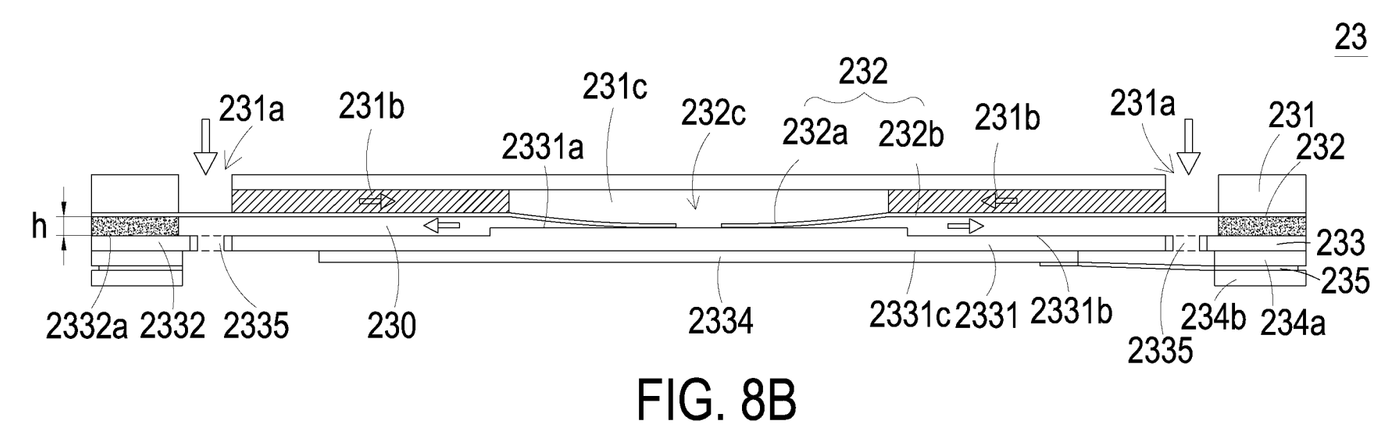
Figure 8C:
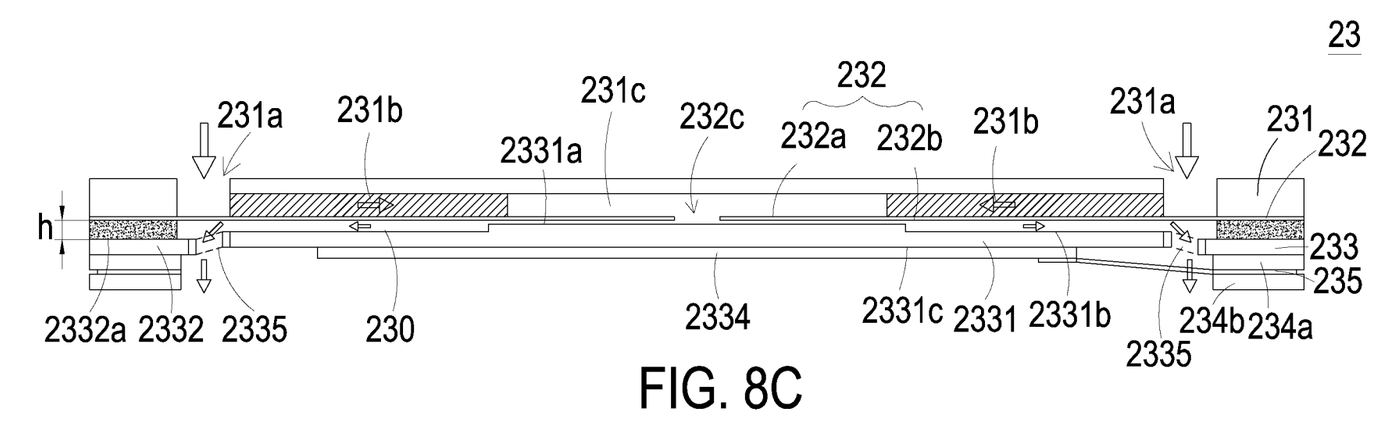
Figure 8D:
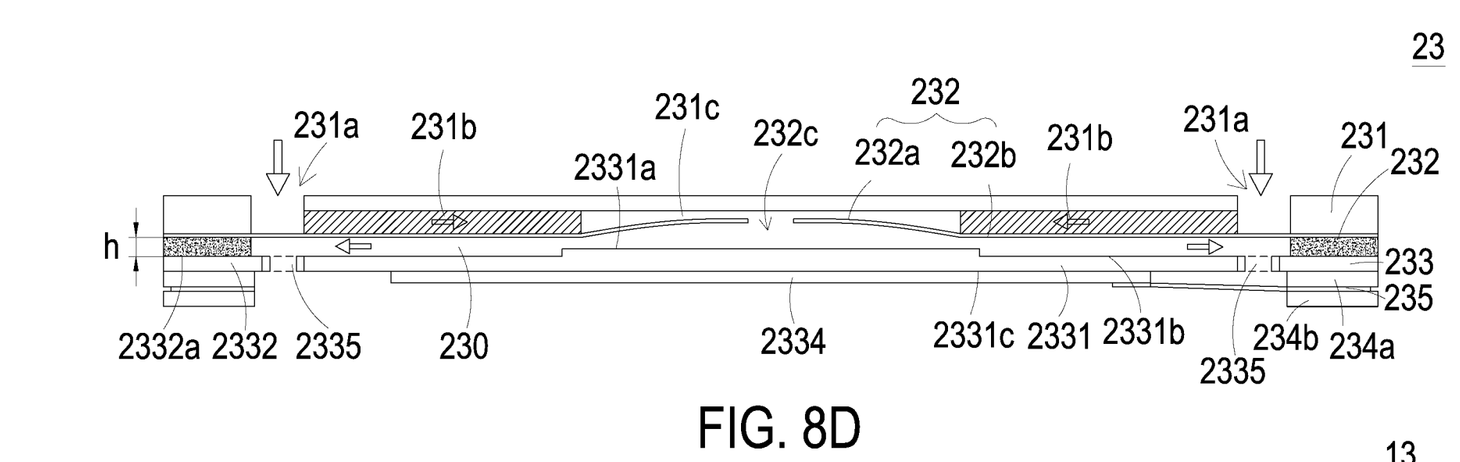
Figure 8E:
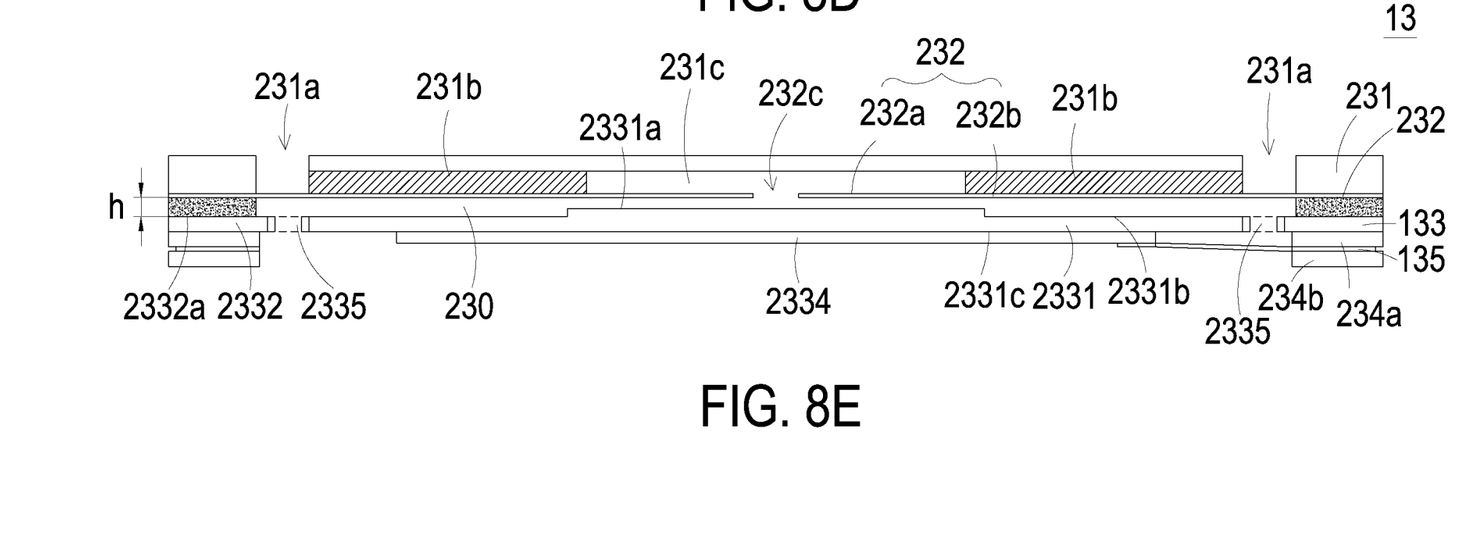

FIGS. 8A to 8E schematically illustrate the actions of the gas transportation actuator according to the embodiment of the present disclosure. Please refer to FIG. 5A, FIG. 5B, FIG. 7 and FIGS. 8A to 8E. The actions of the gas transportation actuator 23 will be described as follows. When the gas transportation actuator 23 is enabled, the piezoelectric actuator 233 vibrates along a vertical direction in a reciprocating manner by using the bracket 2333 as a fulcrum. Please refer to FIG. 8A, the piezoelectric actuator 233 vibrates downwardly in response to the applied voltage. Since the resonance plate 232 is light and thin, the resonance plate 232 vibrates along the vertical direction in the reciprocating manner in resonance with the piezoelectric actuator 233. More specifically, a region of the resonance plate 232 spatially corresponding to the central cavity 231c of the gas inlet plate 231 is also subjected to a bending deformation. The region of the resonance plate 232 corresponding to the central cavity 231c of the gas inlet plate 231 is the movable part 232a of the resonance plate 232. When the piezoelectric actuator 233 deforms downwardly during vibration, the movable part 232a of the resonance plate 232 is subjected to the bending deformation because the movable part 232a of the resonance plate 232 is pushed by the gas and vibrates in response to the piezoelectric actuator 233. In response to the downward deformation of the piezoelectric actuator 233 during vibration, the gas is fed into the at least one inlet 231a of the gas inlet plate 231. Then, the gas is transferred to the central cavity 231c of the gas inlet plate 231 through the at least one convergence channel 231b. Then, the gas is transferred through the central aperture 232c of the resonance plate 232 spatially corresponding to the central cavity 231c, and introduced downwardly into the first chamber 230. As the piezoelectric actuator 233 is enabled, the resonance of the resonance plate 232 occurs. Consequently, the resonance plate 232 vibrates along the vertical direction in the reciprocating manner continuously. As shown in FIG. 8B, during the vibration of the movable part 232a of the resonance plate 232 at this stage, the movable part 232a moves down to contact and attach on the bulge 2331a of the suspension plate 2331 of the piezoelectric actuator 233, and a distance from the fixed part 232b of the resonance plate 232 to a region of the suspension plate 2331 except the bulge 2331a remains the same. Owing to the deformation of the resonance plate 232 described above, a middle communication space of the first chamber 230 is closed, and the volume of the first chamber 230 is compressed. Under this circumstance, the pressure gradient occurs to push the gas in the first chamber 230 moving toward peripheral regions of the first chamber 230 and flowing downwardly through the vacant space 2335 of the piezoelectric actuator 233. Referring to FIG. 8C, the movable part 232a of the resonance plate 232 returns to its original position when the piezoelectric actuator 233 deforms upwardly during vibration. Consequently, the volume of the first chamber 230 is continuously compressed and the piezoelectric actuator 233 is vibrated upwardly to generate the pressure gradient which makes the gas in the first chamber 230 continuously pushed toward peripheral regions. Meanwhile, the gas is continuously fed into the at least one inlet 231a of the gas inlet plate 231, and transferred to the convergence chamber formed in the central cavity 231c. Then, as shown in FIG. 8D, the resonance plate 232 moves upwardly, which is cause by the resonance of upward motion of the piezoelectric actuator 233. That is, the movable part 232a of the resonance plate 232 is also vibrated upwardly. Consequently, it decreases the current of the gas from the at least one inlet 231a of the gas inlet plate 231 into the central cavity 231c. At last, as shown in FIG. 8E, the movable part 232a of the resonance plate 232 has returned to its original position. As the embodiments described above, when the resonance plate 232 vibrates along the vertical direction in the reciprocating manner, the gap h between the resonance plate 232 and the piezoelectric actuator 233 is helpful to increase the maximum displacement along the vertical direction during the vibration. In other words, the configuration of the gap h between the resonance plate 232 and the piezoelectric actuator 233 can increase the amplitude of vibration of the resonance plate 232. Consequently, a pressure gradient is generated in the gas channels of the gas transportation actuator 23 to facilitate the gas to flow at a high speed. Moreover, since there is an impedance difference between the feeding direction and the exiting direction, the gas can be transmitted from the inlet side to the outlet side. Consequently, the gas transportation is achieved. Even if a gas pressure (which may impede the gas flow) exists at the outlet side, the gas transportation actuator 23 still has the capability of pushing the gas to the gas channel while achieving the silent efficacy. The steps of FIGS. 8A to 8E may be done repeatedly. Consequently, gas circulation is generated in which the ambient gas is transferred from the outside to the inside by the gas transportation actuator 23.

From the above descriptions, the present disclosure provides a gas detecting device. The first gas sensor of the gas detecting device has better capability for measuring the first gas. The first gas sensor measures the target gas when the gas transportation actuator is non-actuated and actuated, and transmits the first gas measured information to the data storage device. The second gas sensor of the gas detecting device has better capability for measuring the second gas. The second gas sensor measures the target gas when the gas transportation actuator is non-actuated and actuated, and transmits the second gas measured information to the data storage device. The data processor accesses the first gas measured information and the second gas measured information from the data storage device, and performs a cross comparison among the information stored in the gas database, the first gas measured information and the second gas measured information so that the concentration of the first gas is calculated. Therefore, the gas detecting device may measure the concentration of a single gas, which is mixed in a gas mixture, without separating the single gas from the gas mixture beforehand. In addition, the actuating-and-sensing module includes a miniature gas sensor and miniature gas transportation actuator so that the volume of the gas detecting device is reduced and the gas detecting device is convenient to carry.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A gas detecting device for measuring a target gas containing a first gas and a second gas, comprising:
    an actuating-and-sensing module comprising a first gas sensor, a second gas sensor and a gas transportation actuator, wherein the gas transportation actuator guides the target gas to the first gas sensor and the second gas sensor for measurement;
    a driving controller configured to control actuations and non-actuations of the first gas sensor, the second gas sensor and the gas transportation actuator;
    a data storage device having a gas database, which stores reference information relative to a gas consisting of the first gas, a gas consisting of the second gas and a gas mixture including the target gas measured by the first gas sensor, and stores reference information relative to the gas consisting of the first gas, the gas consisting of the second gas and the gas mixture including the target gas measured by the second gas sensor; and
    a data processor configured to calculate gas concentrations in the target gas,
    wherein the first gas sensor measures the target gas and transmits first gas measured information to the data storage device, the second gas sensor measures the target gas and transmits second gas measured information to the data storage device, and the data processor calculates a concentration of the first gas and a concentration of the second gas in the target gas by comparing the reference information stored in the gas database, the first gas measured information and the second gas measured information.

2. The gas detecting device according to claim 1, wherein the first gas sensor is a semiconductor gas sensor.

3. The gas detecting device according to claim 1, wherein the second gas sensor is a semiconductor gas sensor.

4. The gas detecting device according to claim 1, wherein the first gas is acetone.

5. The gas detecting device according to claim 1, wherein the second gas is ethanol or hydrogen.

6. The gas detecting device according to claim 1, further comprising a display module for displaying information of the concentration of the first gas or information of the concentration of the second gas.

7. The gas detecting device according to claim 1, further comprising a transmission module for transmitting information of the concentration of the first gas or information of the concentration of the second gas.

8. The gas detecting device according to claim 7, wherein the transmission module is at least one selected from the group consisting of a wired transmission module and a wireless transmission module.

9. The gas detecting device according to claim 8, wherein the wired transmission module is at least one selected from the group consisting of a USB transmission module, a mini-USB transmission module and a micro-USB transmission module.

10. The gas detecting device according to claim 8, wherein the wireless transmission module is at least one selected from the group consisting of a Wi-Fi transmission module, a Bluetooth transmission module, a radio frequency identification transmission module and a near field communication transmission module.

11. The gas detecting device according to claim 7, wherein the transmission module is in communication with an external device, wherein the external device is at least one selected from the group consisting of a cloud system, a portable device and a computer system.

12. The gas detecting device according to claim 1, wherein the gas transportation actuator comprises:
    a gas inlet plate having at least one inlet, at least one convergence channel and a central cavity defining a convergence chamber, wherein the at least one inlet allows the gas to flow in, and wherein the convergence channel is disposed corresponding in position to the inlet and guides the gas from the inlet toward the convergence chamber defined by the central cavity;
    a resonance plate having a central aperture and a movable part, wherein the central aperture is aligned with the convergence chamber and the movable part surrounds the central aperture; and
    a piezoelectric actuator aligned with the resonance plate, wherein a gap is formed between the resonance plate and the piezoelectric actuator to define a first chamber, so that the gas from the at least one inlet of the gas inlet plate is converged to the central cavity along the at least one convergence channel and flows into the first chamber through the central aperture of the resonance plate when the piezoelectric actuator is enabled, whereby the gas is further transferred through a resonance between the piezoelectric actuator and the movable part of the resonance plate.

13. The gas detecting device according to claim 12, wherein the piezoelectric actuator comprises:
    a suspension plate having a first surface and a second surface, wherein the suspension plate is permitted to undergo a bending vibration;
    an outer frame arranged around the suspension plate;
    at least one bracket connected between the suspension plate and the outer frame for elastically supporting the suspension plate; and
    a piezoelectric plate, wherein a length of a side of the piezoelectric plate is smaller than or equal to a length of a side of the suspension plate, and the piezoelectric plate is attached on the first surface of the suspension plate, wherein when a voltage is applied to the piezoelectric plate, the suspension plate is driven to undergo the bending vibration.

14. The gas detecting device according to claim 13, wherein the suspension plate is a square suspension plate and has a bulge.

15. The gas detecting device according to claim 12, wherein the piezoelectric actuator comprises a first insulation plate, a conducting plate and a second insulation plate, wherein the gas inlet plate, the resonance plate, the piezoelectric actuator, the first insulation plate, the conducting plate and the second insulation plate are stacked sequentially.

16. The gas detecting device according to claim 1, wherein the first gas measured information includes gas information of the target gas measured by the first gas sensor as the gas transportation actuator is non-actuated and gas information of the target gas measured by the first gas sensor as the gas transportation actuator is actuated, and wherein the second gas measured information includes gas information of the target gas measured by the second gas sensor as the gas transportation actuator is non-actuated and gas information of the target gas measured by the second gas sensor as the gas transportation actuator is actuated.

17. The gas detecting device according to claim 16, wherein the data storage device has the gas database, which stores reference information relative to the first gas, the second gas and the gas mixture measured by the first gas sensor as the gas transportation actuator is non-actuated, reference information relative to the first gas, the second gas and the gas mixture measured by the second gas sensor as the gas transportation actuator is non-actuated, reference information relative to the first gas, the second gas and the gas mixture measured by the first gas sensor as the gas transportation actuator is actuated, and reference information relative to the first gas, the second gas and the gas mixture measured by the second gas sensor as the gas transportation actuator is actuated.

18. A gas detecting device for measuring at least one target gas containing at least one first gas and at least one second gas, comprising:

at least one actuating-and-sensing module comprising at least one first gas sensor, at least one second gas sensor and at least one gas transportation actuator, wherein the gas transportation actuator guides the target gas to the first gas sensor and the second gas sensor for measurement;

at least one driving controller configured to control actuations and non-actuations of the first gas sensor, the second gas sensor and the gas transportation actuator;

at least one data storage device having at least one gas database, which stores reference information relative to a gas consisting of the first gas, a gas consisting of the second gas and a gas mixture including the target gas measured by the first gas sensor, and stores reference information relative to the gas consisting of the first gas, the gas consisting of the second gas and the gas mixture including the target gas measured by the second gas sensor; and at least one data processor configured to calculate at least one concentration of the target gas, wherein the first gas sensor measures the target gas and transmits at least one first gas measured information to the data storage device, the second gas sensor measures the target gas and transmits at least one second gas measured information to the data storage device, and the data processor calculates a concentration of the first gas and a concentration of the second gas in the target gas by comparing the reference information stored in the gas database, the first gas measured information and the second gas measured information.

* * * * *